(12) United States Patent
Tiollais et al.

(10) Patent No.: US 6,225,458 B1
(45) Date of Patent: May 1, 2001

(54) PROCESS FOR THE PRODUCTION OF DNA COMPRISING THE GENOME OF THE HEPATITIS B VIRUS AND VECTOR INCLUDING IT

(75) Inventors: Pierre Tiollais; Alex Fritsch; Christine Pourcel, all of Paris; Patrick Charnay, Boulogne, all of (FR)

(73) Assignees: Institut Pasteur; Institut National de la Santa et de la Recherche Medicale, both of Paris (FR)

( * ) Notice: Subject to any disclaimer, the term of this patent is extended or adjusted under 35 U.S.C. 154(b) by 0 days.

(21) Appl. No.: 08/347,162

(22) Filed: Nov. 23, 1994

Related U.S. Application Data

(63) Continuation of application No. 07/608,618, filed on Nov. 6, 1990, now abandoned, which is a continuation of application No. 07/399,403, filed on Aug. 18, 1989, now abandoned, which is a continuation of application No. 06/785,499, filed on Oct. 8, 1985, now abandoned, which is a continuation-in-part of application No. 06/395,672, filed on Jul. 6, 1982, now abandoned, which is a continuation of application No. 06/104,835, filed on Dec. 18, 1979, now abandoned.

(30) Foreign Application Priority Data

Dec. 18, 1978 (FR) .................................................. 78 35588

(51) Int. Cl.$^7$ .................................................. A61K 39/29
(52) U.S. Cl. .......................... 536/23.72; 536/25.3; 435/5; 435/6; 435/69.1; 435/69.3; 424/189.1
(58) Field of Search ................... 435/5, 6, 69.1, 435/91, 32, 69.3, 70.1, 172.1, 172.3, 320.1, 235.1; 536/23.1, 23.72, 25.3; 424/189.1

(56) References Cited

U.S. PATENT DOCUMENTS 4,237,224 * 12/1980 Cohen et al. .......................... 435/68
4,935,235 * 6/1990 Rutter et al. .......................... 424/88
5,196,194 * 3/1993 Rutter et al. .
6,110,706 8/2000 Thoma .

OTHER PUBLICATIONS

Hrusha et al., J. Virol., 21(2): 666–672 (1977).*
Galibert et al, Nature, vol. 281, Oct. 25, 1979, pp. 646–650.*
Valenzuela et al, Nature, vol. 280, Aug. 30, 1979, pp. 815–819.*
Burrell et al, Nature, vol. 279, May 3, 1979, pp. 43–47.*
Fritsch et al., C.R. Acad. Sc. Paris, Ser. D. 287 (16): 1453–1456 (Dec. 18, 1978).*
Summers, et al., *Biol. Abstracts,* 66 (12): 72159 Dec. 15, 1978.*
Leder, et al., *Science,* 196: 175–177 (1977).*
Summers et al., *Proc. Natl. Acad Sci USA,* 72(11): 4597–4601 (1975).*
Blumberg, *Science,* 197: 17–25 (1977).*
Murray, Molecular Cloning of Recombinant DNA, Academic Press, New York, Scott et al., Editors, 133, 144–146 (1977).*
Scott et al., Editors, 133, 144–146 (1977).*

* cited by examiner

*Primary Examiner*—Laurie Scheiner
(74) *Attorney, Agent, or Firm*—Finnegan, Henderson, Farabow, Garrett & Dunner, L.L.P.

(57) ABSTRACT

The invention relates to a process for producing DNA corresponding to that of the DNA of the virus of B hepatitis. It comprises cloning in bacteria the latter DNA, previously repaired by means of the corresponding precursor nucleotides in the presence of a polymerase. The invention also relates to vectors containing said cloned DNA in their genomes. The cloned DNA is useful as a probe for detecting the presence of the virus of B hepatitis in biological samples, particularly blood or plasma. Its expression in bacteria provides a hybrid protein containing a protein fragment having vaccinating properties against hepatitis B.

30 Claims, 1 Drawing Sheet

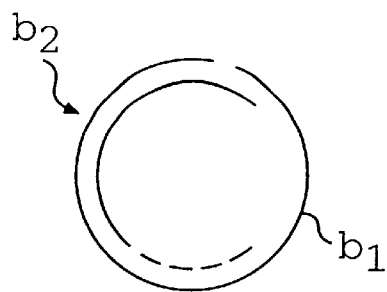
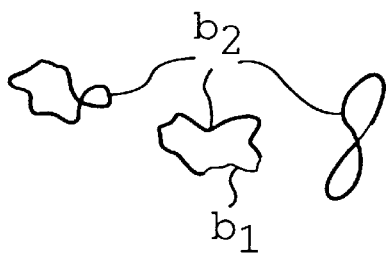
FIG. 1    FIG. 2
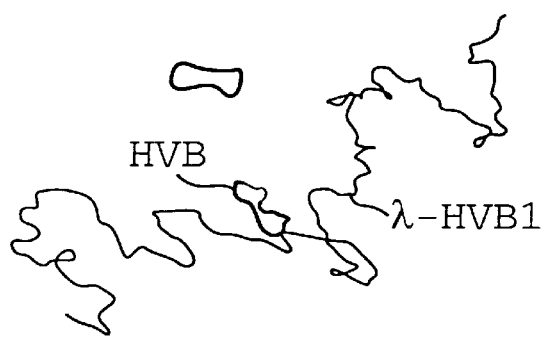
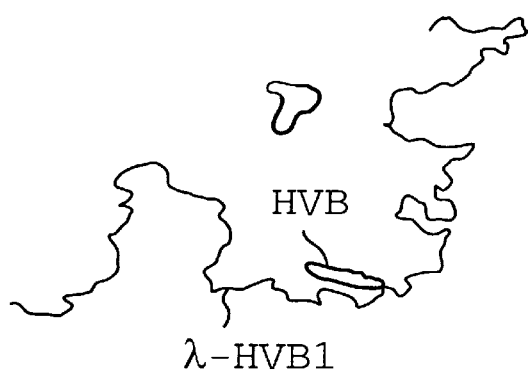
FIG. 3    FIG. 4
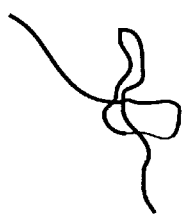
FIG. 5    FIG. 6

PROCESS FOR THE PRODUCTION OF DNA COMPRISING THE GENOME OF THE HEPATITIS B VIRUS AND VECTOR INCLUDING IT

This application is a continuation, of application Ser. No. 07/608,618, filed Nov. 6, 1990, now abandoned which is a continuation of application Ser. No. 07/399,403, filed Aug. 18, 1989, now abandoned, which is a continuation of application Ser. No. 06/785,499, filed Oct. 8, 1985, now abandoned, which is a continuation-in-part of application Ser. No. 06/395,672, filed Jul. 6, 1982, now abandoned, which is a continuation of application Ser. No. 06/104,835, filed Dec. 18, 1979, now abandoned.

The invention relates to a process for the production of a DNA (desoxyribonucleic acid) comprising the genome characteristic of that of the B hepatitis virus. It also relates to DNAs -of which a fragment is constituted by a double strand DNA corresponding to that of viral B hepatitis. Lastly it relates to vectors and compositions including such DNAs, for taking advantages of their biological properties.

B hepatitis is a frequent viral disease, more particularly in tropical Africa, in Southeast Asia and in the Far East where about 10% of the people are carriers of the surface viral antigen also designated as HBs antigen.

Though the infection is often manifested by an acute form without sequelae, it can also be at the origin of a chronic hepatitis, of cirrhosis and even of fatal hepatic necrosis. This explains the importance of studies devoted to the biology of the virus, and the recent development of a vaccine whose efficiency has been demonstrated on patients and members of the personnel of hemodialysis centers (Ph. MAUPAS, A. GOUDREAU, P. COURSAGET, J. DRUCKER and Ph. BAGROS, Intervirol., 10, 1978, 196–208). The Dane particle D. S. DANE, C. H. CAMERON and M. BRIGCS, Lancet. 1970, p. 695–698) is at present considered as the etiological viral agent. This particle, which can be detected by observation with the electron microscope, has a diameter of 42 nm. The patient's serum in the preicteric phase contains up to $10^9$ or even $10^{10}$ of it per milliliter. It possesses an envelope (Australia antigen or HBs antigen), a capsid (HBc antigen), an endogenic polymerase and a DNA molecule (J. L. Melnick, G. R. DREESMAN and F. B. HOLLINGER, Sc. amer., 237, 1977, p. 44–52). Under observation with the electron microscope, the genome appears as a bicatenary DNA ring possessing a monocatenary region, whose length varies from one molecule to the next (J. SUMMERS, A. O'CONNELL and I. MILLMAN, Proc. Nat. Acad. Sc., 72, 1975, p 4597–4601, hereafter referred to as "SUMMERS" and W. S. ROBINSON, Ann. rev. Microbiol., 1977, 31:357–377, hereafter referred to as "robinson". This ring is constituted by two intertwined linear molecules of unequal lengths (as shown diagrammatically in FIG. 1). It is the smallest viral genome known in mammals. The longest strand contains about 3,200 bases. The endogen polymerase DNA can be used to repair in vitro the single strand region ($b_1$ in FIG. 1) of the shortest strand (T. A. LANDERS. H. B. GREENBERG and W. S. ROBINSON, J. Virol., 23, 1977, p. 368–376, hereafter referred to as "LANDERS").

Yet when the genome is repaired in vitro, as disclosed in the articles of SUMMERS, ROBINSON and LANDERS, small strands of DNA are formed in situ along the monocatenary region of the genome. However, these new strands do not connect to form a single strand along the full length of the monocatenary region, SUMMERS also discloses that the DNA polymerase reaction on the Dane particle resulted in a "fully double-stranded product consist(ing of a series of newly synthesized strands 50–500 nucleotides in length duplexed with the unlabeled strand". LANDERS discloses that the "DNA polymerase reaction "closes the single stranded region, resulting in molecules with uniform double-stranded length and a remaining S1-susceptible site (a nick or gap)". ROBINSON noted, regarding the nature of the DNA product of the in vitro endogenous polymerase reaction, that the ends of the repaired portions of the open strand do not appear to be joined to make closed circular DNA, although the single-stranded gaps appear to be closed by the endogenous DNA polymerase reaction. The circular molecules after the DNA polymerase reaction as before have a nuclease S1-sensitive site, and no closed circular DNA is detected by alkaline sucrose gradient sedimentation or equilibrium centrifugation in CsCl density gradient containing ethidium bromide.

Thus it was clearly established in the prior art that in vitro polymerase-repaired DNA derived from the genomes of hepatitis B virus still contained monocatenary regions, i.e. nuclease S1 susceptible sites. As a matter of fact it was well known in the art that the nuclease S1 enzyme can cleave DNA only in areas of monostranded portions and not in the double-stranded portions.

Study of the virus is however at present made particularly difficult by reason of the difficulties of supplies of serum containing Dane particles. Even a rich serum does not permit the preparation of large amounts of DNA (of the order of 1 γ of DNA per volume of 500 ml of serum). It is hence necessary to collect serums of various origin corresponding to several genetic variants (J. P. SOULIER and A. M. COUROUCE-PAUTY, Vox Sang. 25, 1973, p. 212–235), which renders precarious a study of the primary structure of the genome. The presence of the single strand region makes difficult, moreover the establishment of a physical map by restriction enzymes.

The problem of the isolation of relatively large amounts of viral particles attains a still increased importance, when it is desired to have available sufficient amounts of viral particles, more particularly of their HBs antigens, which appear to carry a surface antigen (protein) having vaccinating properties. The present methods of vaccination, if they have demonstrated their efficiency, are not however absolutely devoid of drawbacks. In particular, preparations of HBs, used as a vaccine, may contain antigen components coming from hepatic cells, which can be the origin of an auto-immune response (B. S. BLUMBERG, Science, 197, 1977, p. 17–24).

It is therefore an object of the invention notably to overcome these difficulties more particularly to provide a process enabling the production of DNA of B hepatitis virus (or of the Dane particle), in sufficient amounts for the realization of the above-mentioned studies, and in a state of purity such that its use can be contemplated; even for therapeutic uses.

The invention takes advantage of the fact that the DNA of the Dane particle possesses, after in vitro "repair" in the presence of precursor nucleotides and of a polymerase, a single recognition site with regard to certain endonucleases, notably restriction enzymes, such as the enzyme EcoRI or Xho.

The process of producing a DNA comprising the genome characteristic of that of the DNA of the B hepatitis virus is characterized by the cloning in a bacterium of a double strand DNA, formed from the B hepatitis virus DNA, notably after repair of the latter in vitro as indicated above. This double strand DNA will be denoted below as DNA- HVB. Preferably, the polymerase used is endogenous polymerase of the B hepatitis virus itself.

Preferably, the DNA to be cloned has, previously, been cleaved by an endonuclease such as defined above, notably by the restriction enzyme EcoRI.

To carry out the cloning, recourse is advantageously had to a vector, notably a phage or plasmid, in which the double strand DNA, previously cleaved at its single site, will have first been inserted.

By way of example of a phage enabling the easy cloning of the double strand DNA first opened by EcoRI, may be mentioned λgtWES. λB (P. LEDER, D. TIEMEIER and L. ENQUIST, SCIENCE, 196 (1977) pp. 175–177) which only comprises two EcoRI sites (EcoRI λ1 and EcoRI λ2). The latter enable the insertion of the whole of the DNA of the B hepatitis virus in the genome of this phage, instead and in place of the fragment inside this virus and previously situated between these two EcoRI sites.

It is naturally self-evident that any other vector comprising two EcoRI sites, or even a single EcoRI site, in a part unessential for its own replication, may be used for the same purposes.

Thus the cloning process according to the invention can include the following essential steps:
- the repair of the DNA of the B viral hepatitis, in the presence of precursor nucleotides and of a polymerase to form DNA-HVB;
- the cleavage of the DNA-HVB by the enzyme selected, notably EcoRI;
- the cleavage of the DNA of the vector, recovery of the portions of this DNA (two or three according as the vector includes one or two EcoRI sites), separation and isolation, notably by ultracentrifugation of the two parts of this DNA, which contained in particular respectively the head and tail genes of the phage and the replication genes of the phage (the two operations which precede being feasible simultaneously);
- the mixing of these two parts of the DNA vector and of the DNA-HVB and their reaction in the presence of DNA-ligase, notably such as T4DNA-ligase;
- the transfection or transformation of a culture of host bacteria by the products obtained and, after incubation of the culture,
- the recovery of phages, the extraction of their DNA recombinants, denoted below by λ-HVB1, which then contain DNA-HVB inserted in their genomes and, optionally, the treatment of the latter by the EcoRI enzyme and the isolation notably by ultracentrifugation, of the DNA-HVB, which is detectable by electrophoresis on an agarose gel, due to the fact that it migrates as the slowest fraction and the size of which can then be evaluated at about 3,200 pairs of bases.

Hence novel products are obtained which are of direct use in several fields. The DNAs thus produced, before or after separation of the DNA-HVB, notably by cleavage with EcoRI, are usable as a probe for the in vitro diagnosis of the presence in biological samples of the B-hepatitis virus. To this end, these DNAs can be marked in any manner known in itself by a radio element. The use of such labeled DNAs is particularly advantageous in that it does not require considerable blood samples in persons in whom the presence of the B hepatitis virus is suspected.

By way of example, the interest which attaches to this use for study of contagious cases of B hepatitis or of the detection of the B hepatitis virus treated in hemodialysis centers, can be stressed. In the same way, this method of diagnosis is suited to the checking of blood samples which are to be involved in blood transfusions (or blood plasma or serum).

The invention also relates, by way of novel product, to the vectors in which a double strand DNA corresponding to that of viral hepatitis is inserted. In another mode of application of the invention, it is possible to induce the expression of the vectors, as indicated above, in a bacterium, in order to induce the synthesis of a hybrid protein containing the HBs antigen in particular, for the study and for the preparation of vaccines with regard to B viral hepatitis.

With this in view, it may be advantageous to use as a vector a modified λ bacteriophage comprising in combination:
- mutations having the effect of preventing or retarding the expression of the late genes, particularly of regulating the production of the proteins necessary for encapsidation of this modified DNA in a bacterium notably *E. Coli*, provided with suppressors of said mutations;
- a DNA fragnent comprising a part at least of the Z gene of *E. Coli* and a promotor of the lactose operon (or of an analogous bacterial operon) inserted in a nonessential part of the genome of the phage and
- a site of cleavage by an endonuclease in the abovesaid part of the Z gene, to the exclusion of any other cleavage site by the same endonuclease in the above said modified DNA.

Advantageously, the bacterial operon concerned is *E. coli* lactose operon, the mutations of the abovesaid late genes affect the Q and S genes and the single cleavage site is a EcoRI site.

Such a phage is disclosed in "Molec. Gen. Gent." 170, pp. 171–178(1979).

The manufacture of the abovesaid hybrid protein containing the protein corresponding to a DNA-HVB can then proceed as follows. It comprises infecting by said modified phage a bacterium, notably *E. coli*, not provided with suppressors of the mutations of the late genes of this phage, causing the bacterial strain, if necessary in the presence of a β-galactosidase inducer, the hybrid protein being then recoverable from the cellular proteins formed.

If necessary, the vector used (whether it relates to the vector identified above by way of example or any other phage or plasmid vector) may be modified to ensure the reading in the correct phase of the DNA-HVB inserted in this vector. This can be carried out notably by resorting to the technique consisting of inserting in the vector concerned either two pairs, or four pairs of supplementary bases between the initiation point of the translation of the DNA fragment whose expression is sought and the first pair of bases of the recognition site proximal to the restriction enzyme, notably EcoRI, which is intended to constitute the linkage between the corresponding part of the vector and the proximal end of the DNA-HVB which must be inserted. The added pairs of bases must naturally be such that there are not introduced into the vector triplets of bases which would form a "nonsense" codon whose effect would be to interrupt the translation. There is thus obtained that the pairs of bases which in the first vector form respectively the first pairs of bases of each of the successively translated codons, become in at least a part of the two other vectors, respectively the second and third pairs (or vice versa) of the codons Whose translation will be effected in the same host, previously transfected or transformed by these other vectors. It is thus possible to have a set of vectors enabling the three possible reading phases.

Starting from the first vector including an EcoRI site at a predetermined distance from the initiation point of the translation, it is possible to obtain one of the two other above-indicated vectors, for example by applying the process which comprises:

cutting the first vector by means of the EcoRI enzyme at the level of this site, collecting that of the two phage fragments which comprises the initiation point of the translation, trimming the monocatenary strand of its EcoRI cohesive end by means of a suitable endonuclease, for example S1 endonuclease, recombining the thus-modified fragment, at the level of the free end formed with a fragment such as that named "linker" of the formula

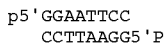

p5'GGAATTCC
CCTTAAGG5'P which itself possesses a recognition site for the EcoRI restriction enzyme, producing the digestion of the modified vector fragment in the presence of EcoRI, which leads to the production of a vector fragment in which the first pair of bases of the EcoRI cohesive end is from then on shifted by two pairs of additional bases with respect to the position that it occupied previously with respect to the initiation point of the translation, and lastly recombining this thus-modified fragment with the other, notably in the presence of a DNA-ligase, notably T4DNA-ligase.

The operation which has just been described can be repeated a second time to produce an additional similar shifting leading to the production of the third possible reading phase.

After insertion of the DNA-HVB in each of these three vectors, it is understood that one of these three vectors will be in any event adapted to be translated correctly by the suitable bacteria-hosts, with consequently the production of a hybrid protein containing that which corresponds to DNA-HVB.

Other characteristics of the invention will appear also in the course of the description which follows of an example of cloning of the genome of the B hepatitis virus in the λgtWES. λB phage.

Reference will be made to the drawings, in which:

FIG. 1 is the diagrammatic representation of a natural DNA-HVB, already referred to in the preamble;

FIG. 2 is a diagram derived from a photograph of three DNA-HVB molecules taken by an electron microscope, of which two are partly monocatenary;

FIGS. 3, 4, 5, and 6 are reproductions drawn from photographs taken under the electron microscope of heteroduplexes between recombinant of DNA of λ phage and that of DNA of viral hepatitis, on the one hand, and of DNA derived directly from Dane particles, on the other hand.

FIG. 1 shows diagrammatically a viral DNA, such as obtained from a Dane particle. It comprises a single strand region $b_1$ and a double strand region $b_2$.

These regions $b_1$ and $b_2$ are marked in the diagrams of FIG. 2 by respectively thin and thicker lines.

1) Purification and repair of the DNA of the B hepatitis virus (DNA-HVB).

400 milliliters of serum rich in Dane particles, distributed in 12 fractions of 25 milliliters, were deposited on saccharose gradients 10–30% (weight/volume) in 10 mM Tris-HCl buffer at pH 8, 10 mM EDTA, 1 M NaCl (TEN Buffer). The centrifugation was effected in a BECKMAN SW27 rotor at 5° C. at 25,000 rpm for 15 hours. Each deposit (containing the Dane particles), was taken up in 0.5 ml of TEN buffer and treated by ultrasound. The suspension (6 ml) was deposited on two saccharose gradients 10–30% and centrifuged in a BECKMAN SW50-1 rotor at 5° C. at 50,000 rpm for 2 hours. The deposits were taken up again in 1 ml of TEN buffer, containing CsCl so as to obtain a density of 1.23 g/ml. This suspension was centrifuged in a BECKMAN SW60 rotor at 20° C. at 55,000 rpm for 15 hours. The gradient was collected in a fraction of 50 µl. The detection of the Dane particles, was done by assay of the endogen polymerase from aliquots of 1 µl. The polymerase activity was detected by measurement of the incorporation of ATP and TTP $\alpha^{32}$ P in an acid precipitatable material described by W. S. ROBINSON (Ann. Rev. Microbiol., 31, 1977) or by T. A. LANDERS et Coll. (J. Virol., 23, 1977, p.368–376).

The fractions in which the incorporation of $^{32}$p was at a maximum had a density of 1.23 g/ml. These fractions (containing the Dane particles) were labelled under the same conditions by a mixture of ATP and TTP $\alpha^{32}$p, having a specific activity 10 times less (this to avoid degradation of the DNA). These fractions were incubated for 1 hour at 37° C. in the presence of pronase (10 mg/ml) and of sodium dodecyl sulfate (1%) and then the DNA was extracted by two successive treatments with a phenol-chloroform mixture (1 vol/1 vol). The DNA was precipitated by the addition of 2 volumes of Ethanol at –20° C., then dissolved in 100 µl of TEN buffer. The concentration of DNA was determined by taking into account the specific activity of the triphosphate precursors, the proportion of single stranded DNA which is on the average 30% and the fact that the endogen polymerase DNA repairs about one half of the single stranded region. The determination of the DNA concentration was confirmed by electrophoretic analysis on agarose gel. The 100 µl (corresponding to 400 ml of plasma) contained about 1 µg of DNA. The examination under the electronic microscope showed that the preparation contained in fact circular DNA of expected length and in which most of the molecules possess a single strand region, of variable length. The proportion of linear molecules of the same length as the circular DNA was about 10%.

2°) In vitro manufacture of recombinants between DNA-HVB and two fragments of the λgtWES. B.

30 ng of DNA-HVB mixed with 500 ng of vector fragment (which corresponds to a molecular ratio close to 1) and were treated by EcoRI endonuclease. Hydrolysis of the DNA-HVB in the presence of the DNA vector enabled the dilution by the latter of possible contamination nuclease activities. After hydrolysis, the fragments were separated by electrophoresis on a polyacrylamide gel (gel gradient having concentrations of acrylamide varying from 2.5 to 7.5%). The fractions obtained were concentrated by chromatography on hydroxylapatite as described previously (TIOLLAIS et al. FEBS.LETTERS, 48 (1974) 96–100). The concentrates obtained were dialysed against a 50 mM Tris-HCl solution at pH 7.5, containing 60 mM of sodium chloride.

Ligation of the fragments then followed by the technique described by MURRAY & MURRAY, NATURE, 251 (1974), 474–481, except for the following modifications. In particular, the DNA solutions contained 30 ng/µl of DNA (the molar ratio between the vector fragments and the fragments to be inserted being comprised between 2 and 6) within a Tris-HCl buffer, at pH 7.5, and 60 mM of sodium chloride. These solutions were heated for 5 minutes at 50° C., to dissociate the cohesive ends. The components identified hereafter were then introduced into the mixture to obtain final concentrations of respectively 10 nM MgCl$_2$, 10 nM of dithiothreitol, 0.1 mM ATP and 50 μg per milliliter of bovine albumin serum. A ligase polynucleotide T4 was then added (notably that produced by MILES LABORATORIES, LTD) and the medium was incubated at 0° C. for 20 hours.
3°) Cloning in the strain C600 recBC rk⁻mk⁻.

The transfection of the strain identified above was carried out according to the method described by CAMERON & Coll., Proc. Natl. Acad. Sci. U.S.A., 72 (1975) 3416–3420). The strain was then spread over lactose MacConkey medium. Eight independent clones were amplified in the strain DP50 Sup F. The DNA was then cleaved by the EcoRI enzyme and the fragments were analysed by electrophoresis on agarose gel. In all cases, the latter revealed the presence of an EcoRI fragment which migrated as the slowest fraction. The latter was formed by DNA-HVB, and its size could be estimated at about 3200 pairs of bases.
4°) Identification among the cloned DNAs of the fragment corresponding to DNA-HVB.

The DNA of the recombinant bacteriophage (λ-HVB 1) was hybridised with the initial DNA-HVB in the ratio of three molecules of DNA-HVB per one molecule of DNA λ-HVB 1.

The heteroduplex molecules observed contained a bicatenary loop of a size equal to that of the bicatenary DNA-HVB and situated at the expected position in the genome of the bacteriophage. Two types of loops were observed; either an entirely bicatenary loop or a loop carrying a monocatenary region situated in the central region of the inserted EcoRI fragment (FIGS. 3 and 4). When the two strands of the vector were paired, two loops were observed (FIGS. 5 and 6).

Different arguments show that the cloned DNA is indeed DNA-HVB. After digestion of the DNA of the hybrid lambda bacteriophage (HVB-1) by the EcoRI endonuclease, electro phoretic analysis shows the presence of a fragment having the length of DNA-HVB. In the same way the heteroduplex loops observed after hybridization have the same length. The existence of bicatenary loops carried by the monocatenary DNA proved that the DNA which was inserted was circular before the cleavage by the EcoRI enzyme. The presence of two types of loops (entirely and partly bicatenary) proves that the original DNA was formed of two paired chains and of equal sizes. The characteristics fit well with those of the B hepatitis genome.

The abundance of heteroduplex molecules possessing the expected structure is important. This establishes that the fragment cloned was not a DNA contaminant, since in the preparation of DNA-HVB the electron microscope enables a less than 1% contamination to be detected.

The DNA clone represents apparently the whole of the genome of Dane particles. In fact, the structure of the heteroduplex molecules indicated that the most fragile part of the DNA-HVB namely the monocatenary region, has been indeed incorporated. In addition, the length of the cloned DNA shows that if the latter were shorter than the DNA of the Dane particles the difference in length would be less than the errors in measurements namely about 150 pairs of bases. All of the foregoing results confirm also the existence of a single EcoRI restriction site in the DNA-HVB.

The thus-cloned DNA-HVB can be labelled in vitro, notably with a radioactive isotope $^{32}$p. It is advantageously applied as a probe to detect the presence of Dane particles, for example in human serum. It is possible to this effect to resort to any conventional DNA-DNA hybridization technique.

The invention finally also concerns a method for the production of a hybrid protein containing a protein fragment having vaccinating activity against hepatitis B which-comprises introducing the above defined vector in bacteria, causing the latter to translate at least the part of said vector which contains the DNA corresponding to that of hepatitis B and recovering said hybrid protein.

As itself evident and as also emerges from the foregoing, the invention is in no way limited to those of its embodiments and applications which have been more especially contemplated; it encompasses on the contrary all modification, notably those in which recourse is had for the cloning according to the invention to other genetic modifications of the DNA of B hepatitis virus.

We claim:

1. A recombinant DNA molecule consisting of a phase or plasmid cloning vector and an HBV DNA insert wherein said HBV DNA insert is full length, fully double-stranded HBV DNA linearized by EcoRI or Xho and further wherein said recombinant DNA molecule is fully double-stranded.

2. The recombinant DNA molecule of claim 1, wherein said cloning vector is a phage vector.

3. The recombinant DNA molecule of claim 1, wherein said cloning vector is a plasmid vector.

4. The recombinant DNA molecule as claimed in claim 1, wherein said recombinant DNA molecule is λ-HVB1.

5. The recombinant DNA molecule as claimed in claim 1, wherein said cloning vector is λgtWES.λB.

6. A process for producing a fully double stranded cloned recombinant DNA molecule, wherein said process comprises:
   providing DNA of hepatitis B virus, wherein said DNA is the genome of hepatitis B virus following in vitro polymerase repair and cleavage with a restriction enzyme selected from the group consisting of EcoRI and Xho;
   ligating said DNA to a phase or plasmid cloning vector to produce a recombinant DNA molecule;
   introducing said recombinant DNA molecule into bacteria;
   causing the bacteria to replicate the recombinant DNA molecule to produce a cloned recombinant DNA molecule; and
   recovering from the bacteria said cloned recombinant DNA molecule; and
   wherein said cloned recombinant DNA molecule is fully double-stranded.

7. The process for producing a fully double-stranded cloned recombinant DNA as claimed in claim 6, wherein said cloned recombinant DNA molecule is λ-HVB1.

8. The process for producing a fully double-stranded cloned recombinant DNA as claimed in claim 6, wherein said cloning vector is λgtWES.λB.

9. A purified full-length HBV DNA in fully double-stranded form.

10. A probe comprising the full-length HBV DNA as claimed in claim 9.

11. The probe as claimed in claim 10, wherein said probe is radiolabelled.

12. A method of detecting the presence of viral hepatitis virus in a biological sample comprising
   a) providing a probe as claimed in claim 10;
   b) contacting a biological sample to be assayed with said probe under hybridization conditions; and
   c) detecting hybridization.

13. The method of detecting the presence of viral hepatitis virus as claimed in claim 12, wherein said biological sample is selected from the group consisting of blood, plasma, or serum.

14. The probe as claimed in claim 10, wherein said probe is labeled.

15. A recombinant DNA molecule comprising the HBV DNA of claim 9.

16. A phage or plasmid cloning vector comprising the HBV DNA of claim 9.

17. A recombinant DNA molecule comprising full-length, fully double-stranded HBV DNA linearized by EcoRI or Xho and further wherein said recombinant DNA molecule is fully double-stranded.

18. A probe comprising the recombinant DNA molecule as claimed in claim 17.

19. The probe as claimed in claim 18, wherein said probe is radiolabelled.

20. A method of detecting the presence of viral hepatitis virus in a biological sample comprising a) providing a probe as claimed in claim 18;
   b) contacting a biological sample to be assayed with said probe under hybridization conditions; and
   c) detecting hybridization.

21. The method of detecting the presence of viral hepatitis virus as claimed in claim 20, wherein said biological sample is selected from the group consisting of blood, plasma, or serum.

22. The probe as claimed in claim 18, wherein said probe is labeled.

23. A probe comprising one strand of the recombinant DNA molecule as claimed in claim 17, wherein said strand includes fully repaired monocatenary region.

24. The probe as claimed in claim 23, wherein said probe is radiolabelled.

25. A method of detecting the presence of viral hepatitis virus in a biological sample comprising a) providing a probe as claimed in claim 23;
   b) contacting a biological sample to be assayed with said probe under hybridization conditions; and
   c) detecting hybridization.

26. The method of detecting the presence of viral hepatitis virus as claimed in claim 25, wherein said biological sample is selected from the group consisting of blood, plasma, or serum.

27. A probe comprising one strand of full-length HBV DNA, wherein said strand includes fully repaired monocatenary region.

28. The probe as claimed in claim 27, wherein said probe is radiolabelled.

29. A method of detecting the presence of viral hepatitis virus in a biological sample comprising a) providing a probe as claimed in claim 27;
   b) contacting a biological sample to be assayed with said probe under hybridization conditions; and
   c) detecting hybridization.

30. The method of detecting the presence of viral hepatitis virus as claimed in claim 29, wherein said biological sample is selected from the group consisting of blood, plasma, or serum.

* * * * *

UNITED STATES PATENT AND TRADEMARK OFFICE
CERTIFICATE OF CORRECTION

PATENT NO. : 6,225,458 B1
DATED : May 1, 2001
INVENTOR(S) : Pierre Tiollais et al.

Page 1 of 1

It is certified that error appears in the above-identified patent and that said Letters Patent is hereby corrected as shown below:

<u>Title page,</u>
Item [73], Assignees, "la Santa" should read -- la Sante --.

<u>Column 8, claim 1,</u>
Line 15, "phase" should read -- phage --.

Signed and Sealed this

Twelfth Day of February, 2002

Attest:

JAMES E. ROGAN
*Attesting Officer*  *Director of the United States Patent and Trademark Office*